(12) United States Patent
Beil et al.

(10) Patent No.: US 9,153,423 B2
(45) Date of Patent: Oct. 6, 2015

(54) METHODS AND DEVICES FOR CALIBRATING THE MOBILITY AXIS OF AN ION MOBILITY SPECTRUM

(71) Applicant: Bruker Daltonik GmbH, Bremen (DE)

(72) Inventors: Andreas Beil, Leipzig (DE); Michael Blaschke, Metzingen (DE)

( * ) Notice: Subject to any disclaimer, the term of this patent is extended or adjusted under 35 U.S.C. 154(b) by 0 days.

(21) Appl. No.: 14/487,285

(22) Filed: Sep. 16, 2014

(65) Prior Publication Data
US 2015/0129760 A1    May 14, 2015

(30) Foreign Application Priority Data

Aug. 6, 2013 (EP) ................................. 13003928

(51) Int. Cl.
  H01J 49/14   (2006.01)
  H01J 49/00   (2006.01)
  G01N 27/64   (2006.01)
  G01N 27/62   (2006.01)
  G01N 33/00   (2006.01)

(52) U.S. Cl.
  CPC .......... *H01J 49/0009* (2013.01); *G01N 27/622* (2013.01); *G01N 33/0006* (2013.01)

(58) Field of Classification Search
  CPC ... G01N 27/624; G01N 27/622; H01J 49/004; H01J 49/04; H01J 49/0404; H01J 49/06; H01J 49/105
  USPC ............. 250/288, 281, 282, 287, 423 R, 424; 315/111.8
  See application file for complete search history.

(56) References Cited

U.S. PATENT DOCUMENTS

| 8,742,363 B2* | 6/2014 | Munchmeyer et al. .... 250/423 P |
| 2004/0232326 A1 | 11/2004 | Guevremont et al. |
| 2005/0167583 A1* | 8/2005 | Miller et al. .................. 250/290 |
| 2005/0173629 A1* | 8/2005 | Miller et al. .................. 250/290 |
| 2007/0176092 A1* | 8/2007 | Miller et al. .................. 250/288 |
| 2013/0153762 A1 | 6/2013 | Muenchmeyer et al. |

FOREIGN PATENT DOCUMENTS

| EP | 0447158 A2 | 9/1991 |
| WO | 2009088461 A2 | 7/2009 |

* cited by examiner

Primary Examiner — Nikita Wells
(74) Attorney, Agent, or Firm — Robic, LLP

(57) ABSTRACT

Methods and devices are provided for calibrating the mobility axis of an ion mobility spectrum and determining the mobility characteristic of ion species from an ion mobility spectrum, in particular for calibrating the drift time axis of an ion mobility spectrum acquired by a drift type ion mobility spectrometer (IMS). An ion mobility spectrometer uses an ion source that comprises a first ionization region which is fluidly coupled to a sample source, a second ionization region which is spatially separated from the first ionization region and fluidly coupled to a calibrant reservoir, and electrical means for controlling the transfer of sample ions from the first region into the second ionization region or into a third region of the ion source wherein the third region is fluidly coupled to the first and second ionization region and located closer to a mobility analyzer than the first and second ionization region.

15 Claims, 7 Drawing Sheets

METHODS AND DEVICES FOR CALIBRATING THE MOBILITY AXIS OF AN ION MOBILITY SPECTRUM

BACKGROUND OF THE INVENTION

1. Field of the Invention

The present invention relates to methods and devices for calibrating the mobility axis of an ion mobility spectrum and for determining the mobility characteristic of ion species from an ion mobility spectrum, in particular for calibrating the drift time axis of an ion mobility spectrum acquired by a drift type ion mobility spectrometer (IMS).

2. Description of the Related Art

Ion mobility spectrometry is based on characterizing chemical substances by the gas-phase mobility of their ionic species under the influence of an electric field. It has been known as an analytical technique since the late 1960s and early 1970s. Ion mobility spectrometers (IMS) operated at ambient pressure are highly sensitive for detecting substances at low concentrations in ambient air and from vaporized samples, and have been successfully utilized for the detection of environmental pollutants, explosives and illicit drugs in the civil sector as well as for the detection of chemical warfare agents (CWAs) in the military sector.

Drift-type IMS are most commonly used in commercial instruments and are based on following principles: a gas sample or vapor from a heated sample is introduced into an ion source with an ionization region to form ions. The ions are introduced from the ion source into a drift region in a pulsed or modulated manner and migrate under the influence of a homogeneous static electric field through a drift tube, normally against a counter flow of dry carrier gas. An ion detector provided at the end of the drift tube is used to measure the drift time it takes for the ionic species to pass through the drift tube. There are other types of IMS operated at ambient pressure, for example Differential Mobility Spectrometry (DMS, also known as Field Asymmetric Ion Mobility Spectrometry, FAIMS) and the aspiration-type IMS.

The gas-phase substances from a sample source (e.g., a desorber or direct sampling of ambient air) are commonly introduced by a carrier gas into the ion source of the IMS and are most commonly ionized by chemical ionization (CI). The carrier gas of an IMS is typically purified air with only some parts per million (ppm) of water vapor. Electrons emitted for example by a radioactive beta emitter, such as $Ni^{63}$, generate positive nitrogen ions by electron impact ionization and negative oxygen ions by electron attachment of thermalized electrons. The nitrogen and oxygen ions further react with water molecules present as vapor in the carrier gas to generate positive $(H^+(H_2O)_n)$ or negative water cluster ions $(O_2^-(H_2O)_n)$, respectively. These secondary reactant ions react with gas-phase substances by protonation forming positive product ions, or by adduct formation forming negative product ions. The primary oxygen ions may also react with gas-phase substances by de-protonation, electron transfer or adduct formation forming negative product ions. The electrons generating the primary reactant ions can be provided by radioactive as well as by non-radioactive electron sources, such as electrical discharges, electron beam generators and/or UV/X-ray lamps. However, direct ionization of the gas-phase substances by UV and X-ray is also possible.

It is well known that, for drift-type IMS, the measured drift time $t_d$ of an ion species can be calculated in a good approximation from following equation:

$$t_d = \frac{L/E \cdot T_0/T \cdot P/P_0}{K_0}$$

wherein L is the length of the drift tube, E is the homogeneous static electric field strength in the drift tube, $T_0$ is the standard temperature, T is the actual temperature in the drift tube during the measurement, P is the actual pressure in the drift tube during the measurement, Po is the standard pressure and $K_0$ is the reduced mobility of the ion species. The physical characteristic of an ion species together with the properties of the drift gas are combined into the reduced mobility $K_0$ which corresponds to the mobility of the ion species in the drift gas at standard conditions of temperature and pressure. A large value of reduced mobility equates to rapid motion of the ion species in the electric field and thus to a small cross section for collisions with the drift gas. The reduced mobility is the characteristic mobility measure of the ion species to be determined from the measured drift time and experimental parameters. If the aforementioned equation is rearranged to $K_0$ as function of the drift time and experimental parameters, it can serve as a calibration function between the drift time axis of a measured ion mobility spectrum and the mobility axis of a calibrated ion mobility spectrum.

The length of the drift tube and the electric field strength of a drift type IMS are fixed or controlled, respectively. The actual pressure P and temperature T during the measurement are further experimental parameters which need to be determined in order to calculate the reduced mobility $K_0$ from the measured drift time. The temperature can be measured with a simple and inexpensive sensor with reasonable accuracy, whereas measuring the pressure inside the drift tube with a sufficient accuracy needs quite elaborate pressure gauges. The determined experimental parameters can be used to establish a calibration function.

Besides calculating the reduced mobility from the measured drift time and the actual experimental parameters during the acquisition of the ion mobility spectrum, it is well known to utilize a calibrant that is introduced into the ionization region of the IMS ion source together with gas-phase substances from the sample source. The reduced ion mobility of the calibrant ions is known and the drift time of calibrant ions is measured under the actual conditions of the drift type IMS. Under the reasonable assumption that the experimental conditions seen by the calibrant ion and the sample ions are similar through the ion source and drift region, the reduced ion mobility of sample ions can be determined from the measured drift time of the sample ions using the measured drift time of the calibrant ions and their known reduced mobility.

FIG. 1 shows a schematic drawing of an ion mobility spectrometer 1 known from the prior art. The ion mobility spectrometer 1 comprises an ion source 10, an ion mobility analyzer 20 (e.g., a drift type analyzer) fluidly coupled to the ion source 10 and a calibrant reservoir 30. An air sample (or more generally a gas sample to be analyzed) is drawn by gas pump 40 into the ion source 10 at a first inlet 51a from the surroundings. The ion mobility spectrometer 1 comprises an additional inlet 51b and a gas outlet 52. If valve 31 is opened, air from outside is also drawn into calibrant reservoir 30. The gas-phase sample and the calibrant are ionized in the ionization region 11 by a radioactive beta emitter 12 and transferred to the mobility analyzer 20, e.g., by the gas flow generated by gas pump 40. Alternatively, the gas-phase sample and calibrant can be mixed prior to the ion source and introduced into the ion source 10 at a single inlet.

In general, a calibration function provides a relation between the abscissa of a measured ion mobility spectrum (e.g., the drift time in a drift type IMS or the compensation voltage in FAIMS) and a mobility characteristic (e.g., the reduced mobility). The ion mobility generally depends on the actual temperature and pressure in the mobility analyzer. Therefore, the calibration function commonly depends on the actual temperature and pressure.

The international patent application WO 2009/088461 A2 provides an explosive and narcotics detection system using an ion mobility spectrometer. The calibration of the spectrometer depends on the stability of the used calibrant 5-nitrovanilin that is periodically injected together with sample gas into the ionization region of the spectrometer. The calibrant produces a signal with a known drift time and may be used to calibrate the drift times of the sample ions.

The international patent application WO 2010/051241 A1 teaches that calibrants and reactants used in conventional ion mobility spectrometry systems can impair the ability to detect species of interest by suppressing the signal amplitude of the species of interest or having coincident drift times, for example. In order for the IMS to have good sensitivity for the weakly ionized substances, the reactant/calibrant must not interfere with the ionization process or mask the ion's unique drift-time peaks.

The international patent application WO 2008/053181 A1 provides a FAIMS being arranged so that the analyte is subject to different ion chemistries at different locations along the spectrometer.

In view of the foregoing, there is still a need to provide devices for fast and reliable delivery of calibrant ions and methods for accurately calibrating the mobility axis of an ion mobility spectrum and determining the mobility characteristic of ion species from an ion mobility spectrum.

SUMMARY OF THE INVENTION

The invention provides an ion mobility spectrometer (IMS) with an ion source and a mobility analyzer, characterized in that the ion source comprises a first ionization region which is fluidly coupled to a sample source, a second ionization region which is spatially separated from the first ionization region and fluidly coupled to a calibrant reservoir, and electrical means for controlling the transfer of ions from one ionization region into the other ionization region and/or from at least one ionization region into a third region of the ion source. The third region is fluidly coupled to both ionization regions and the mobility analyzer, and is located closer to the mobility analyzer than the first and second ionization region.

The electrical means can be electrically switched between two operating states. In a first state (calibration mode), the transfer of sample ions from the first ionization region into the second ionization region or, respectively, the third region is substantially inhibited by electric fields. In the second state (sample mode), sample ions are transferred by electrical fields and/or a gas flow from the first ionization region towards the mobility analyzer, either by passing the second ionization region or by passing the third region of the ion source. The sample ions can be transferred by an electric drift field and/or by a gas flow. The inhibition of the transfer can be realized by switching of an electric drift field, preferably in combination with a counteracting gas flow, or by applying blocking potentials to electrodes of the first ionization region which are preferably arranged at the exit end of the first ionization region. The sample and calibrant ions can, for example, be generated by an electromagnetic radiation source (e.g., a UV-, VUV- or X-ray source), a radioactive source (e.g., a beta emitter $Ni^{63}$), an electrical discharge or a non-radioactive electron source as described for example in WO 93/11554 A1 or EP 1 070 960 A2. The mobility analyzer can be any type, e.g., a drift type mobility analyzer, a differential mobility analyzer (also known as Field Asymmetric Ion Mobility Analyzer) or the aspiration-type mobility analyzer.

In a first embodiment, the first ionization region, the second ionization region and the mobility analyzer are arranged in series, i.e., the first ionization region is adjacent to the second ionization region and the second ionization region is adjacent to the mobility analyzer. The mobility analyzer can comprise a drift tube which is separated from the second ionization region by a shutter gate and comprises means for establishing a gas flow which is directed from the drift tube through the second ionization region towards the first ionization region. Alternatively, the first ionization region coupled to the sample source can be arranged between the second ionization region coupled to the calibrant reservoir and the mobility analyzer. The ion source can comprise an X-ray tube which is located on the front side of the ion source such that radiation is emitted and passes through the first and the second ionization region along the axis of the drift tube. The photon energy of the emitted X-rays is preferably between 2 and 10 keV, most preferably at 4 keV. However, the ion source of the embodiment may comprise radioactive sources, e.g., beta emitter $Ni^{63}$, which are located in the first and second ionization region.

In a second embodiment, the ion source comprises a third region and further electrical means for controlling the transfer of calibrant ions from the second ionization region into the third region. The electrical means of the second ionization region can be the same as the electrical means of the first ionization region.

The electrical means of the IMS according to the present invention can be one of a Bradbury-Nielson gate, a single apertured electrode, and a grid electrode, which are preferably located at the exit of the first and/or second ionization region. These electrical means are connected to a switchable DC voltage generator that is capable of generating appropriate electric blocking potentials, preferably positive and negative electric DC potentials for subsequently blocking ions of both polarities (positive/negative mode of IMS operation). In case of the Bradbury-Nielson gate the DC voltage generator provides alternating potentials to adjacent grid electrodes such that a dipolar field is generated between adjacent grid electrodes, in particular positive and negative potentials applied to adjacent grid electrodes. The electrical means can also comprise multiple apertured electrodes located along the first and/or second ionization region for generating a switchable electrical drift field therein.

The calibrant reservoir can be filled with one or more calibrants, for example with chlorovanilin and/or a dicarboxylic acid, e.g. oxalic acid or malonic acid. One calibrant is preferably used in negative mode and another calibrant in positive mode. The IMS can also comprise more than one calibrant reservoir, for example each one filled with a different calibrant. The calibrant for positive mode is preferably oxalic acid which has a reasonable vapor pressure at the operating temperature of an IMS so that the calibrant reservoir does not have to be heated by an additional heating element.

The present invention further provides a method for calibrating the mobility axis of an ion mobility spectrum acquired in an ion mobility spectrometer having an ion source and a mobility analyzer, comprising the steps: (a) providing a gas-phase substance from a sample source to a first ionization region of the ion source and a gas-phase calibrant to a second ionization region of the ion source, wherein the first and the second ionization region are spatially separated; (b) switching an electric potential applied to at least one electrode of the first ionization region such that the transfer of sample ions from the first ionization region into the second ionization region or, respectively, into a third region of the ion source is inhibited, wherein the third region is located closer to the mobility analyzer than the first and second ionization region; (c) acquiring a mobility spectrum of calibrant ions generated in the second ionization region wherein the mobility spectrum does not substantially comprise signals of sample ions generated in the first ionization region; and (d) determining a calibration function for the mobility axis from at least one signal of a calibrant ion species and the known mobility of the calibrant ion species. Step (d) can comprise that measured experimental parameters (like the pressure) are adjusted or determined using the determined signal position of the calibrant ion species in the calibrant spectrum, in both cases with the knowledge of the ion mobility of the calibrant ion species. The term "substantially" means that at most 20%, preferably 10% or less and most preferably 1% or less of the signal intensities in the calibration spectrum belong to sample ion signals. The electric potential applied to the electrode of the first ionization region can be switched into the sample mode and an additional combined spectrum comprising calibrant ions and sample ions can be acquired wherein the combined spectrum can be additionally used to determine the signal positions of the calibrant ions.

In a first embodiment, the method can further comprise the following steps: switching the electric potential to release ions from the first ionization region into the third region; acquiring a mobility spectrum comprising signals of calibrant and sample ions; and determining the mobility characteristic for at least one sample ion using the calibration function.

In a second embodiment, the method can further comprise the following steps: switching the electric potential applied to the at least one electrode of the first ionization region to release ions from the first ionization region into the third region; switching an electric potential applied to at least one electrode of the second ionization region such that the transfer of sample ions from the second ionization region into the third region of the ion source is inhibited; acquiring a mobility spectrum substantially comprising signals of sample ions only; and determining the mobility characteristic for at least one sample ion using the calibration function.

The present invention provides a further method for calibrating the mobility axis of an ion mobility spectrum acquired in an ion mobility spectrometer having an ion source and a mobility analyzer, comprising the steps of: (a) providing a gas-phase substance from a sample source to a first ionization region of the ion source and a gas-phase calibrant to a second ionization region of the ion source, wherein the first and the second ionization region are spatially separated; (b) switching an electric potential applied to at least one electrode of the second ionization region such that the transfer of calibrant ions from the second ionization region into the first ionization region is inhibited and acquiring a first mobility spectrum substantially not comprising signals of calibrant ions; (c) switching the electric potential applied to the at least one electrode of the second ionization region such that calibrant ions are released into the first ionization region and acquiring a second mobility spectrum comprising sample and calibrant ions; and (d) determining a calibration function for the mobility axis from at least one signal of a calibrant ion species and the known mobility of the calibrant ion species. The sample spectrum substantially comprising only signals of sample ions can be used to determine the at least one signal of the calibrant ion species in the combined mobility spectrum acquired in step (c), for example by subtracting the (appropriately scaled) sample spectrum from the combined spectrum.

The methods according to the present invention may further comprise that the signal position of a reactant ion species (RIN=reactant ions negative, RIP=reactant ions positive) is utilized to further adjust the calibration function with regard to the humidity of the gas in the mobility analyzer.

A first advantage of the present invention is the capability for fast switching between acquiring sample and calibrant spectra. In the prior art, the gas-phase calibrant is injected together with gas-phase sample into the ion source via a gas inlet. The pneumatic switching and the volume of the tubing between the calibrant reservoir and the ion source and, in particular, the duration of stay of the calibrant in the ion source limits the time needed to switch from a sample spectrum to a calibrant spectrum and back to a sample spectrum. In an IMS according to the present invention, the switching time between sample and calibrant spectra can be less than 1 s and even less than 50 ms. Therefore, the calibration can instantaneously follow the drift of experimental parameters.

A second advantage of preferred embodiments is that the signals of the calibrant spectrum are neither masked nor chemically shifted by substances from the sample source (even at highest sample concentrations) because the generation of sample ions and calibrant ions is spatially decoupled. Therefore, a useful calibrant spectrum can be acquired even at highest target concentrations and contaminations of the ionization region coupled to the sample source. Furthermore, the amount of calibrant introduced into the ion source can be kept at a minimal concentration at which the calibrant ions do not disturb determining the mobility characteristic of sample ions if measured together with sample ions, in particular at low target concentrations.

A third advantage of preferred embodiments is that the signal position of the calibrant ions in the calibrant spectrum can be determined more accurately due to the decoupling. Therefore, the calibration or, respectively, the determination of the actual experimental parameters, in particular the pressure, is improved which results in an improved accuracy for determining the mobility characteristic of the sample ions and thus in an improved identification rate and/or reduced false positive rate for target substances. If a combined spectrum comprising sample and calibrant ions is acquired, the combined spectrum can be processed to eliminate the signals of the calibrant ions using the calibrant spectrum, for example by subtracting the calibrant spectrum from the combined spectrum.

DETAILED DESCRIPTION

Embodiments of the present invention will be described below, by way of example only, with reference to the drawings. It should be noted that the figures are schematic and not drawn to scale. Relative dimensions and proportions of parts of the figures may be shown exaggerated or reduced in size, for the sake of clarity and convenience. In the figures, the same reference signs are used to refer to corresponding or similar elements in modified and different embodiments.

Figure 1:
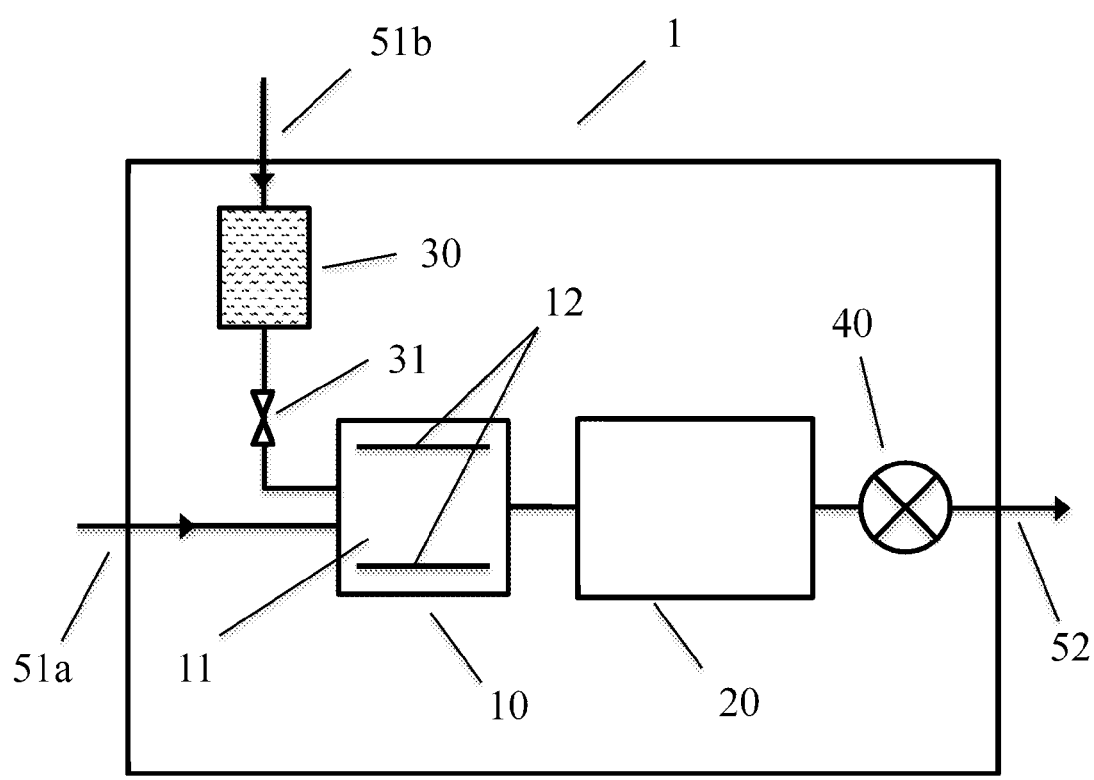
FIG. 1 shows an IMS 1 known from the prior art with an ion source 10 wherein a sample inlet 51a and a calibrant reservoir 30 are fluidly coupled to a single ionization region 11 of the ion source 10.
Figure 2:
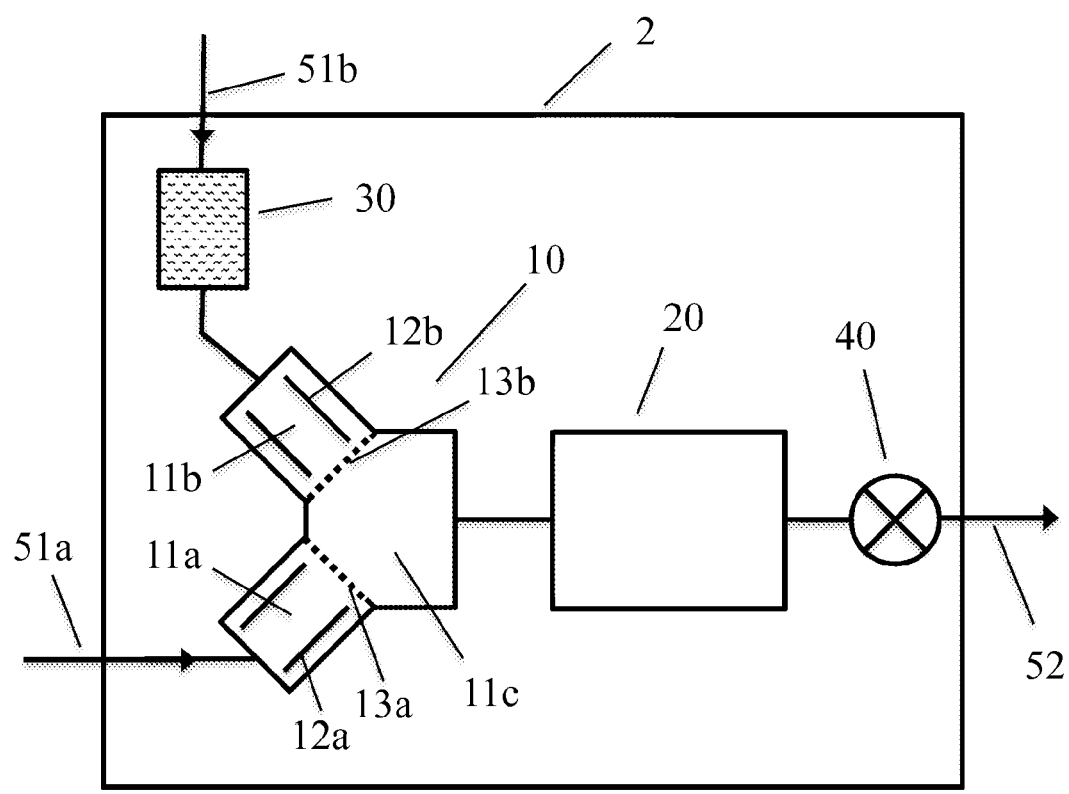
FIG. 2 shows an IMS 2 with an ion source 10 comprising a first ionization region 11a, a second ionization region 11b and a third region 11c wherein both ionization regions 11a, 11b comprise a radioactive source 12a, 12b and are fluidly coupled to the third region 11c.

FIG. 2 shows an ion mobility spectrometer 2 that comprises an ionization source 10, a mobility analyzer 20, a calibrant reservoir 30 and a gas pump 40. The ion source 10 comprises a first ionization region 11a, a second ionization region 11b and a third region 11c wherein both ionization regions 11a, 11b comprise a radioactive source 12a, 12b and are fluidly coupled to the third region 11c. Both ionization regions 11a and 11b are separated from the third region by Bradbury-Nielson grids 13a and 13b which are connected to DC power supplies (not shown). The ion source is operated at atmospheric pressure. The ion mobility analyzer 20 is preferably a commonly used drift-type mobility analyzer, but may also be a filter-type mobility analyzer (DMS=differential mobility spectrometry) or an aspiration-type mobility analyzer.

When pump 40 is operating, an air sample (or more generally a gas sample to be analyzed) is drawn into the ionization region 11a at a first inlet 51a from surroundings. The ion source 10 comprises an additional inlet 51b to which air from outside is also drawn into calibrant reservoir 30. Sample and calibrant ions generated in the first and second ionization region 11a, 11b are drawn by gas flow into the third region 11c and then into the mobility analyzer 20. The air volume drawn in at inlets 51a and 51b is exhausted at outlet 52.

When grid 13a is supplied with alternating potentials, dipolar fields are generated between adjacent grid electrodes such that positive and negative sample and reactant ions are neutralized at gate 13a, i.e., that the transfer of sample ions from the first ionization region 11a into the third region and the mobility analyzer 20 is inhibited. If gate 13b is open, a calibrant spectrum can be acquired in the mobility analyzer 20 which substantially comprises only reactant and calibrant ions from the second ionization region 11b. When gate 13a is opened and gate 13b is blocking the transfer of ions from second ionization region 11b, a sample spectrum can be acquired in the mobility analyzer which substantially comprises only sample and reactant ions from the first ionization region 11a. The calibrant spectrum is utilized to calibrate the mobility axis of the sample spectrum or to estimate the experimental parameters in the mobility analyzer 20 (e.g., the pressure). In some embodiments, both gates 13a, 13b can be opened simultaneously in order to acquire a combined sample, calibrant and reactant ion spectrum.

Figure 3:
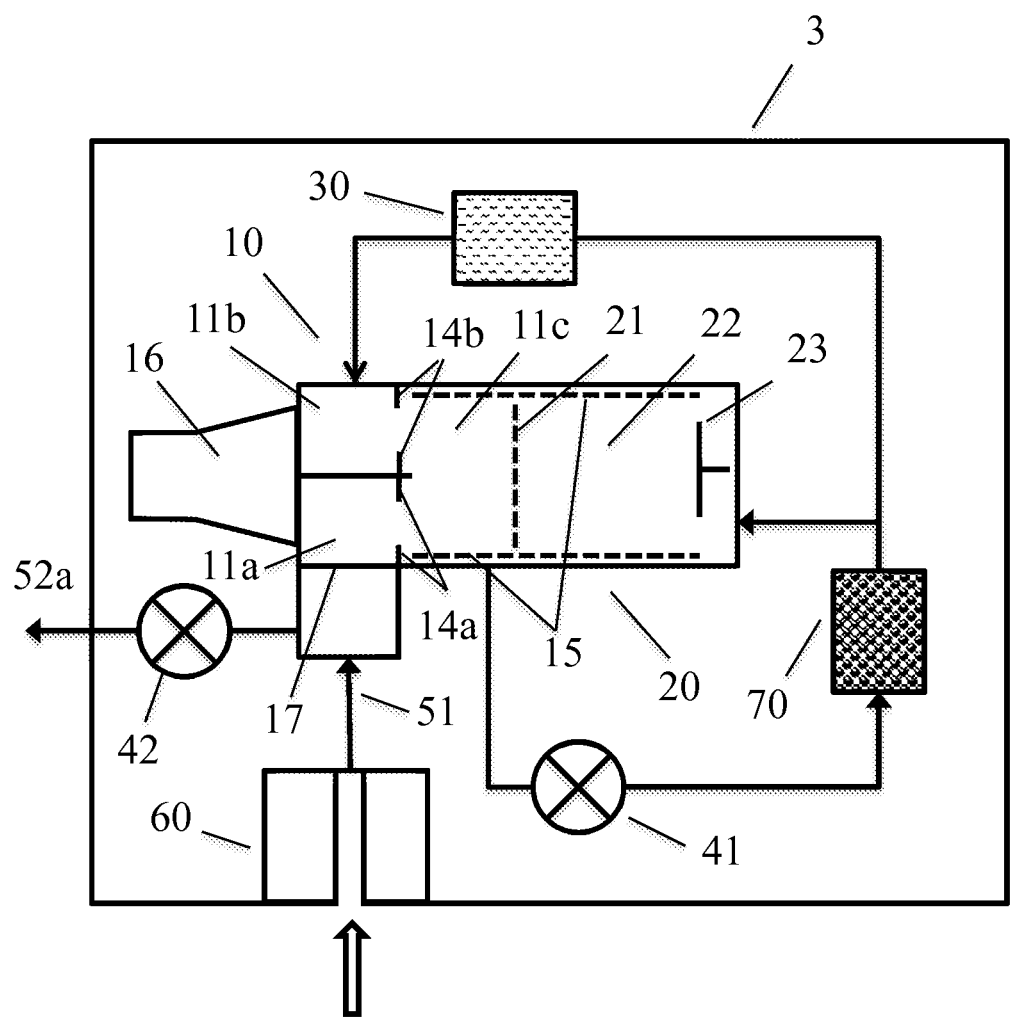
FIG. 3 shows an IMS 3 with an ion source 10 comprising a first ionization region 11a, a second ionization region 11b and a third region 11c wherein a X-ray tube 16 is mounted at the front side of the IMS 3 such that both ionization regions 11a, 11b are provided with ionizing X-ray radiation.

FIG. 3 shows an ion mobility spectrometer 3 that comprises an ionization source 10, a mobility analyzer 20 with a drift tube 22 and an ion detector 23, a calibrant reservoir 30, a first and second gas pump 41, 42, a desorbing unit 60 and a filter 70.

Ion mobility spectrometers are widely-used to detect target substances in the civil sector, such as explosives and illicit drugs. The target substances are usually detected via their vapors. The detection of modern explosives and drugs, in particular, is hampered by the fact that these target substances have a very low vapor pressure and are often enclosed in transport containers. In most cases, direct detection of these target substances in the ambient air is therefore only possible by collecting a large sample volume with subsequent enrichment. However, the surface of baggage, transport containers and clothes as well as skin of the persons doing the packing are usually contaminated with minimal traces of the substances, which are present as condensations from vapors on the surface itself or as particles adhering to the surface of the containers. They have too low vapor pressures to be directly detectable in the ambient air. The surfaces to be investigated are therefore wiped with a sampler, causing condensed substances and particles carrying the substances to be removed from the surface and to adhere to the sampler. Currently, paper, woven fabrics or felt are used as samplers, for instance. After wiping the surface to be investigated, the sampler is transferred into the desorption unit 60 of the IMS 2, where it is heated in order to increase the vapor pressures of the target substances which are sufficient for detection. The desorbing unit 60 is fluidly coupled to the ion source 10 via inlet 51.

The desorbing unit 60 is fluidly coupled to a chamber which is separated from the first ionization region 11a by a semi-permeable membrane 17 made of polysiloxane, for instance. When the desorbing unit 60 is loaded with a sampler and the sampler is heated in there, sample gas is drawn from the desorbing unit 60 into the chamber 11 by pump 42. The semi-permeable membrane 17 is thus flushed from outside with the sample gas. The target substances enter the first ionization region 11a via the semi-permeable membrane 17. The semi-permeable membrane 17 is commonly heated in order to reduce memory effects. The sample gas is exhausted at outlet 52a.

In the closed gas circulating system, gas is pumped from the ion source 10 through the filter 70 into the drift tube 22 of the mobility analyzer 20 and back into the ion source 10 via the calibrant reservoir 30. A counter-flowing clean gas is often used in drift-type mobility analyzers to convectively transport neutral target substances out of the drift tube because neutral substances can react with drifting ions such that the drift time of ions is affected and their ion mobility is determined inaccurately. The circulated gas is continuously cleaned from target substances and freed of moisture in the filter 70. The filter 70 is most commonly an activated charcoal combined with a molecular sieve. The moisture in the ion source 10 is preferably held constant at a level of less than 100 ppm, preferably around 10 ppm. Constant moisture in the ion source 10 and the mobility analyzer is helpful to establish stable conditions for the ionization process and to enable accurate measurement of the mobility, respectively.

The ion source 10 comprises a first ionization region 11a, a second ionization region 11b and a third region 11c which is adjacent to the drift tube 22 and separated from the drift tube 22 by a shutter gate 21 (most commonly a Bradbury-Nielsen grid). As commonly known, the shutter gate 21 is used to release ions to be analyzed in a pulsed or modulated manner into the drift tube 22. The injected ions are detected at the back side of the mobility analyzer 20 by the ion detector 23, commonly a Faraday cup. The drift field inside the drift tube 22 is generated by applying appropriate potentials to a stack of aperture electrodes 15 which extend towards the third region 11c of the ion source 10. Positive or, respectively, negative ions are transferred from the third region 11c of the ion source 10 towards the mobility analyzer 20 by the drift field generated by respective potentials applied to the stack of aperture electrodes 15. The ion source 10 comprises a single X-ray tube 16 which is mounted at the front side and emits X-rays into the ionization region 11a and 11b. The X-rays can ionize the calibrant and sample substance in the ionization regions 11a and 11b or generate photoelectrons to start chemical ionization. The photon energy of the X-ray is between 2 and 10 keV, most preferably 4 keV. The single electrodes 14a and 14b at the exit of the ionization regions 11a and 11b are electrical means for controlling the transfer of ions from the ionization regions 11a and 11b into the third region 11c.

In the calibration mode, a blocking potential is applied to the electrode 11a and a drawing potential is applied to electrode 14b such that only positive (or negative, respectively) reactant and calibrant ions are transferred from the second ionization region 11b into the third region 11c. An appropriate drift field adjusted to the respective polarity of the ions draws them towards the shutter gate 21 and, if the shutter gate 21 is opened, further along the drift tube 22 towards the ion detector 23. The measured ion mobility spectrum comprises reactant ions and calibrant ions of respective polarity, but substantially not ions from the ionization region 11a. This calibrant spectrum is used to determine or to adjust a calibration function of the drift time axis or is used to determine or adjust experimental parameters inside the drift tube 22, e.g., the pressure and humidity. In the sample mode, a sample spectrum substantially without calibrant ions is acquired by switching the potentials at the electrodes 14a and 14b such that a blocking potential is applied to electrode 14b and a drawing potential is applied to electrode 14a. A combined spectrum comprising ions from both ionization regions 11a and 11b can be acquired by applying drawing potentials to both electrodes 14a and 14b.

Figure 4:
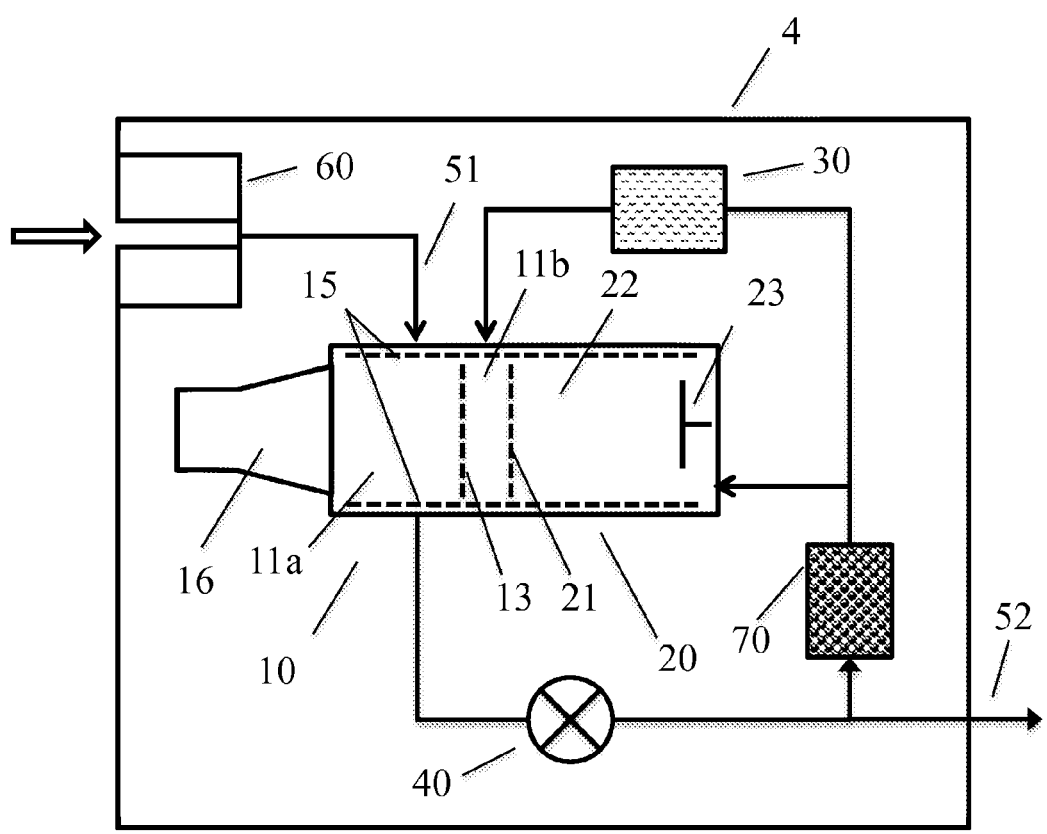
FIG. 4 shows an IMS 4 with an ion source 10 comprising a first and a second ionization region 11a, 11b and a X-ray tube 16 mounted at the front side of the IMS 4 wherein the two ionization regions 11a, 11b are separated by an additional gating grid 13 and arranged in series with a drift tube 22.

FIG. 4 shows an ion mobility spectrometer 4 that comprises an ionization source 10, a mobility analyzer 20 with a drift tube 22 and an ion detector 23, a calibrant reservoir 30, a gas pump 40, a desorbing unit 60 and a filter 70. The calibrant reservoir is preferably filled with oxalic acid, most preferably with oxalic acid and chlorovanilin.

As explained for embodiment of FIG. 3, the surfaces to be investigated are wiped with a sampler, causing condensed substances and particles carrying the substances to be removed from the surface and to adhere to the sampler. After wiping the surface to be investigated, the sampler is transferred into the desorption unit 60 of the ion mobility spectrometer 4, where it is heated in order to increase the vapor pressures of the target substances which are sufficient for detection. The desorbing unit 60 is fluidly coupled to the ion source 10 by inlet 51.

The ion mobility spectrometer 4 comprises an internal gas circulating system. When pump 40 is operating and intake of sample gas from the desorbing unit 60 is disabled by closing inlet 51, gas is pumped from the ion source 10 through the filter 70 into drift tube 22 and into the ion source 10 via the calibrant reservoir 30 which is preferably filled with oxalic acid and chlorovanilin to provide calibrant ions for the positive or negative mode, respectively. The gas in the drift tube 22 flows against the drifting ions to keep sample neutrals away from drift tube 22. When the desorbing unit 60 is loaded with a sampler and heats the sampler, inlet 51 is opened and sample gas is drawn into the ion source 10. The amount of gas drawn into the ion source 10 is exhausted at outlet 52 positioned between the pump 40 and filter 70. The circulating gas drawn out from the ion source 10 is continuously cleaned from substances and freed of moisture in the filter 70. The moisture in the ion source 10 is preferably held constant at a level of less than 100 ppm, preferably around 10 ppm.

The ion source comprises two regions, a first ionization region 11a and a second ionization region 11b. The gas-phase calibrants are injected with the circulating gas into ionization region 11b which is located between first ionization region 11a and the drift tube 22. The second ionization region 11b is separated from the drift tube 22 by a shutter gate 21 (most commonly a Bradbury-Nielsen grid) used to release ions from the second ionization region 11b into the drift tube 22 and start the acquisition of the ion mobility spectrum. The gas-phase sample substances are introduced into the first ionization region 11a which is separated from the second ionization region by an additional shutter gate 13 (e.g., a Bradbury-Nielsen grid). An X-ray tube 16 is mounted at the front side of the ion source 10 such that ionizing X-ray radiation is emitted and passes through the first and the second ionization region 11a, 11b along the axis of the drift tube 22. Sample ions are substantially only generated in the first ionization region 11a because the gas flowing from the drift tube 22 through the second ionization region 11b sweeps sample neutrals back into the first ionization region 11a. A stack of aperture electrodes 15 extends from the first ionization region 11a along the second ionization region 11b and the drift tube 22. The direction of the electrical drift field can be switched to acquire ion mobility spectra in positive and negative mode.

By applying appropriate DC potentials to the aperture electrodes 15, ions of a respective polarity drift from the ion source 10 along the drift tube 22 towards the ion detector 23. In the calibration mode, alternating potentials are applied to the additional shutter gate 13 to neutralize reactant and sample ions drifting towards the additional shutter gate 13. Only reactant ions and calibrant ions from the second ionization region 11b reach the shutter gate 21 and are released into the drift tube 22. A measured ion mobility spectrum comprises reactant ions and calibrant ions of respective polarity, but substantially not ions from the ionization region 11a. This calibrant spectrum is used to determine or to adjust a calibration function of the drift time axis or is used to determine or adjust experimental parameters inside the drift tube 22, e.g., the pressure and humidity. In the sample mode, the additional grid 13 is opened and a combined spectrum comprising sample and calibrant ions from the first and second ionization region 11a, 11b is measured. A pure sample spectrum can be processed from the measured spectra by eliminating the calibrant ion signals in the combined spectrum, for example by subtracting the calibrant spectrum from the combined spectrum accounting for appropriate scaling.

Figure 5:
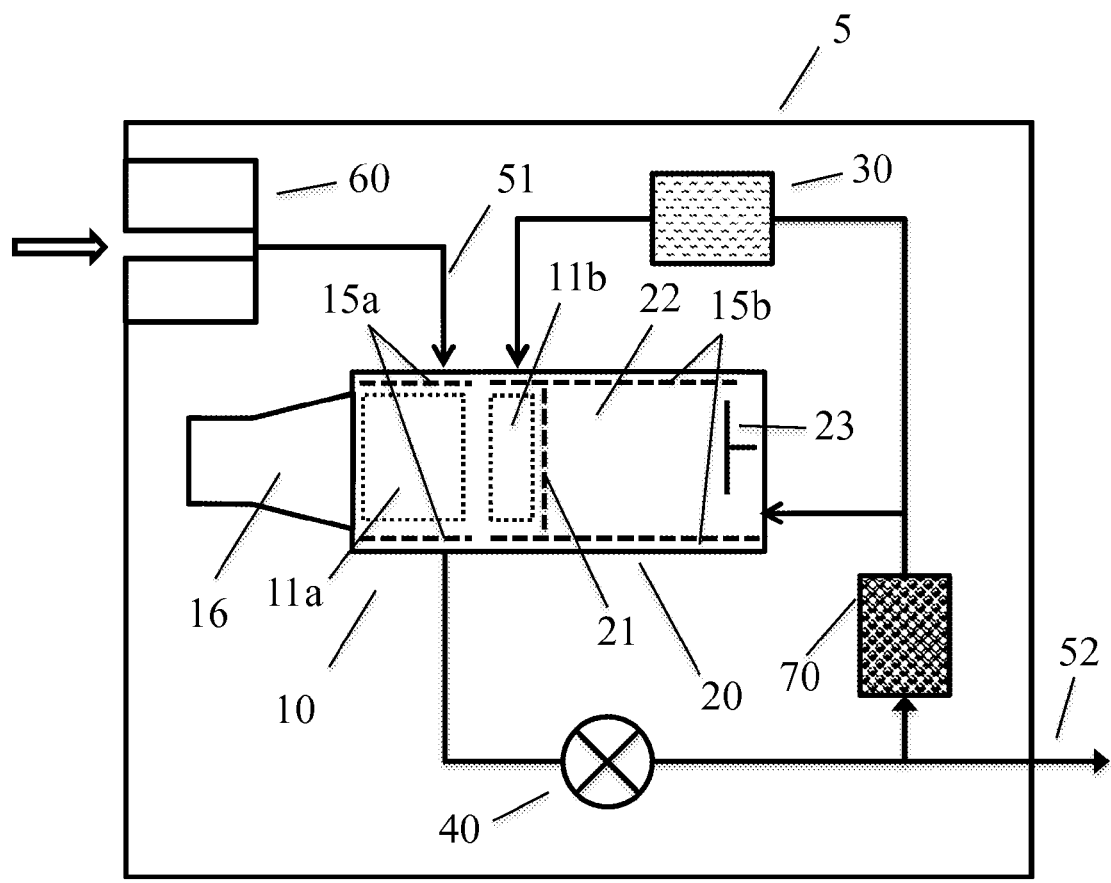
FIG. 5 shows an IMS 5 with an ion source 10 comprising a first and a second ionization region 11a, 11b and a X-ray tube 16 mounted at the front side of the IMS 5 wherein the ionization regions 11a, 11b are arranged in series with a drift tube 22 and each ionization region 11a, 11b comprises a stack of aperture electrodes 15a, 15b for generating drift fields in the respective ionization region 11a, 11b.

FIG. 5 shows an ion mobility spectrometer 5 that comprises an ionization source 10, a mobility analyzer 20 with a drift tube 22 and an ion detector 23, a calibrant reservoir 30, a gas pump 40, a desorbing unit 60 and a filter 70. The calibrant reservoir is preferably filled with chlorovanilin, most preferably with oxalic acid and chlorovanilin.

The embodiment shown in FIG. 5 is similar in design and function compared to embodiment shown in FIG. 4. They are different in that the ion source 10 of IMS 5 does not comprise an additional grid between the first and the second ionization regions 11a and 11b and that aperture electrodes are divided into a first stack 15a and a second stack 15b. The stacks of aperture electrodes are connected to a DC power supply (not shown) that can independently provide DC potentials to the electrode stacks 15a and 15b. The first electrode stack 15a extends only along the first ionization region 11a whereas the second electrode stack 15b extends along the second ionization region 11b and the drift tube 22.

In the calibration mode, the drift field in the ionization region 11a generated by the electrode stack 15a is switched off (or even reversed) such that reactant and sample ions from the ionization region 11a are not driven by an electrical field towards the second ionization region 11b. The gas flowing from the drift tube 22 through the second ionization region 11b keeps sample neutrals as well as sample ions generated in the first ionization region 11a away from entering the second ionization region 11b and thus from being transferred towards the drift tube 22 by the drift field generated by the electrodes stack 15b. Therefore, an ion mobility spectrum acquired in the calibration mode substantially comprises only reactant ions and calibrant ions, but not ions from the ionization region 11a. In the sample mode, a drift field is generated in the first ionization region 11a which draws ions from the first ionization region 11a against the counter flowing gas into the second ionization region 11b where they are transferred together with the calibrant ions towards the shutter gate 21 by the drift field generated by second electrode stack 15b. An ion mobility spectrum acquired in the sample mode contains signals of sample and calibrant ions (combined spectrum). A pure sample spectrum can be processed from the measured spectra by eliminating the calibrant ion signals in the combined spectrum, for example by subtracting the calibrant spectrum from the combined spectrum.

Figure 6A:
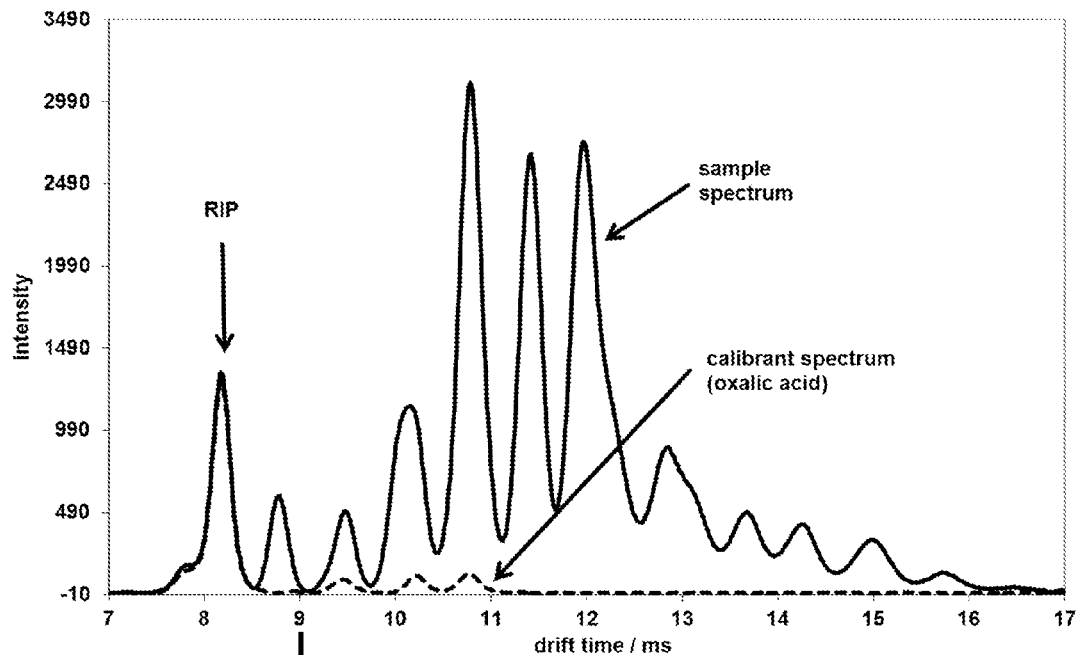
FIGS. 6A and 6B each show a calibrant and sample spectrum acquired in positive mode with the IMS shown in FIG. 4 using oxalic acid as a calibrant.
Figure 6B:
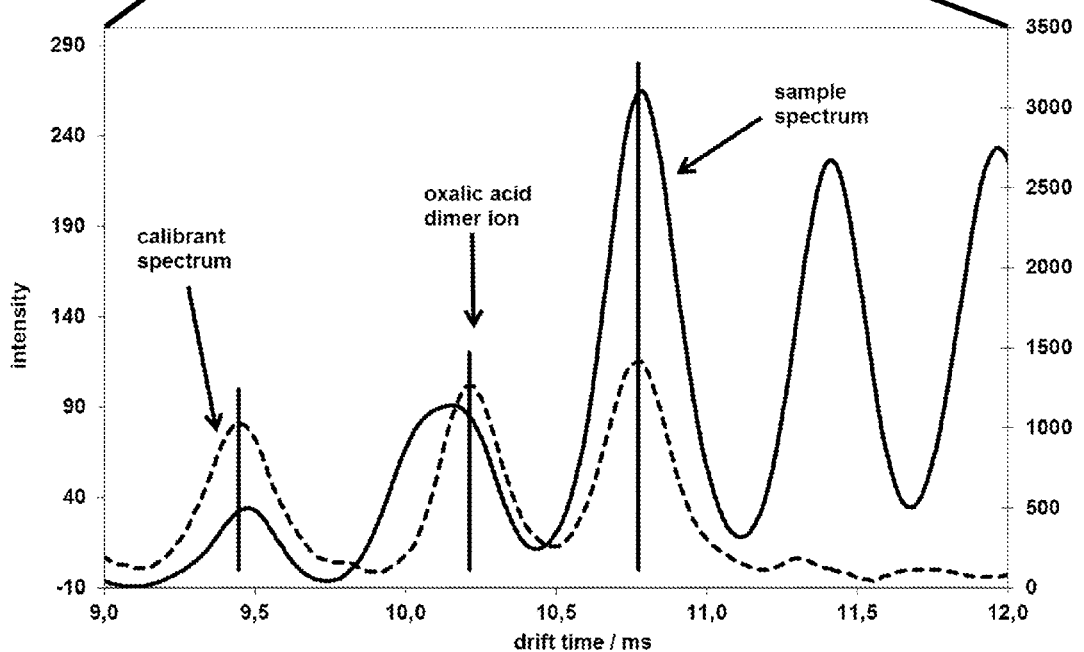

FIGS. 6A and 6B show a calibrant and combined sample spectrum acquired in positive mode with the IMS shown in FIG. 4 using oxalic acid as calibrant. According to the operating principle of the IMS 4, the combined sample spectrum comprises signals of calibrant and sample ions. In this example, a mixture of dinitrotoluene isomers, succinic acid and malonic acid is applied to a swipe and used as sample. The swipe with the dried sample mixture is introduced into desorbing unit 60 of IMS 4. The spectra are acquired according to the sample and calibration mode described above. FIG. 6A shows both spectra over the full drift time range from about 7 ms to 17 ms. The signal of the positive reactant ions (RIP) is located at about 8 ms. The signal intensities in the combined spectrum are much higher than the signal intensities in the calibrant spectrum. FIG. 6B shows a part of the calibrant and combined spectrum between 9 ms and 12 ms wherein the intensity scales of the calibrant and combined spectrum (left and right ordinate) are adjusted accordingly.

The signal of the oxalic acid dimer ion species is indicated in FIG. 6B by an arrow (drift time of 10.24 ms, known reduced mobility $K_0=1.64$ cm$^2$/Vs). The peak position of this ion species is quite independent to conditions of the gas chemistry in the ionization region, e.g., to the humidity and $CO_2$ concentration. The peak positions of other ion species of the oxalic acid, like monomers and monomer adduct ions (such as water, $CO_2$, sample molecules) are not as stable compared to the oxalic acid dimer. In the combined spectrum as shown, the signal of the oxalic acid dimer is superimposed by a signal of a sample ions species having much higher signal intensity. It would not be impossible to (at least precisely) determine the position of the preferred calibrant signal in the combined spectrum. Therefore, the combined spectrum alone cannot be used to calibrate the mobility axis of measured mobility spectra. The decoupled acquisition of the calibrant and combined spectrum according to the present invention allows a fast and reliable calibration of the mobility axis even with overlapping signals and/or, for overloaded samples at high sample concentration, far beyond the dynamic intensity range of the IMS.

Figure 7:
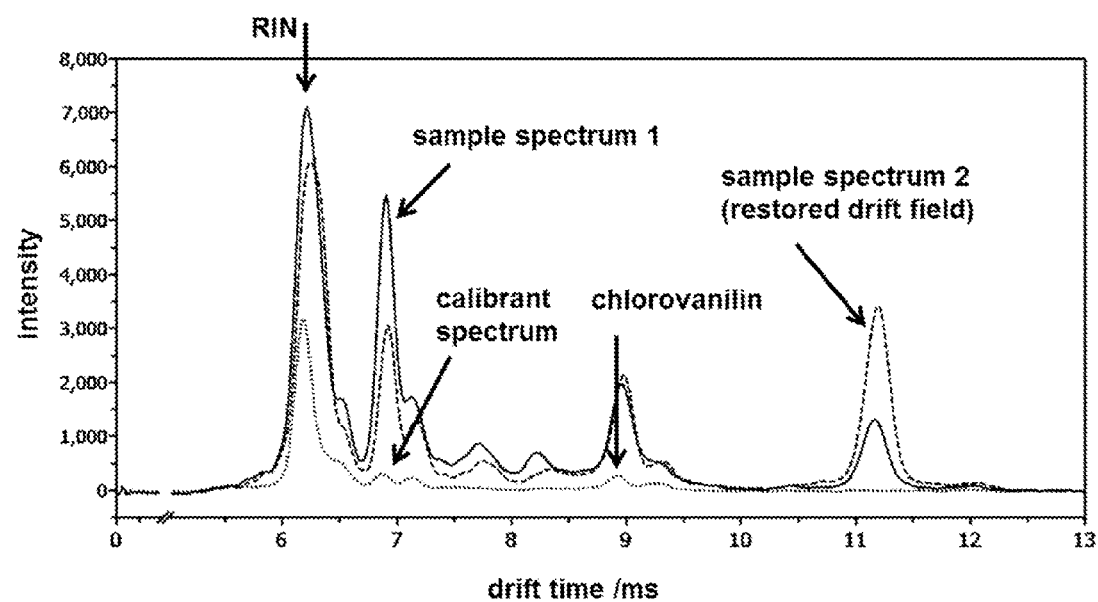
FIG. 7 shows a calibrant and sample spectrum acquired in negative mode with the IMS shown in FIG. 5 using chlorovanilin as a calibrant.

FIG. 7 shows a calibrant and combined spectra acquired in negative mode with the IMS shown in FIG. 5 using chlorovanilin as calibrant. According to the operating principle of the IMS 5, the combined spectra comprise signals of calibrant and sample ions. In this example, phenethyl salicylate is applied on a swipe and used as a sample simulating an artificial contamination. The swipe with the dried sample is introduced into desorbing unit 60 of IMS 5. FIG. 7 shows three measured mobility spectra in positive mode over the drift time range from about 5.5 ms to 12.5 ms. The signal of the negative reactant ions (RIN) is located at about 6.25 ms. The signal intensities of the combined spectra are much higher than the signal intensities of the calibrant spectrum. The signal of the chlorovanilin ion species is indicated by an arrow at drift time of 8.9 ms. Combined spectra and calibrant spectrum are acquired according to the sample and calibration mode described above for IMS 5. After acquiring the first combined spectrum (sample spectrum 1), the drift field in the first ionization region is switched off. The neutrals introduced to the first ionization region 11a and ions generated in the first ionization region 11a are kept away from the second ionization region 11b by the gas flowing from the drift tube 22 through the second ionization region 11b towards the first ionization region 11a. The signal of the chlorovanilin ion species is indicated by an arrow (drift time of 8.9 ms). In the combined spectra as shown, the signal of the chlorovanilin is superimposed by a signal of a sample ions species having much higher signal intensity. It would not be impossible to (at least precisely) determine the position of the preferred calibrant signal in the combined spectra. After acquiring the calibrant spectrum, the drift field in the first ionization region 11a is restored and a second combined spectrum (sample spectrum 2) is acquired. The signal of the phenethyl salicylate ion species again dominates the combined spectrum at the peak position of the calibrant ion species. The drift field is switched in less than 100 ms between the states.

While the invention has been shown and described with reference to a number of embodiments thereof, it will be recognized by those skilled in the art that various changes in form and detail may be made herein without departing from the spirit and scope of the invention as defined by the appended claims.

The invention claimed is:

1. An ion mobility spectrometer with an ion source and a mobility analyzer, the ion source comprising:
   a first ionization region which is fluidly coupled to a sample source,
   a second ionization region which is spatially separated from the first ionization region and fluidly coupled to a calibrant reservoir, and
   an ion transfer system that controls the transfer of ions from one ionization region to the other and/or from at least one ionization region to a third region of the ion source, wherein the third region is fluidly coupled to the first and second ionization regions and located closer to the mobility analyzer than the first and second ionization regions.

2. The ion mobility spectrometer according to claim 1, wherein the first ionization region, the second ionization region and the mobility analyzer are arranged in series.

3. The ion mobility analyzer according to claim 2, wherein the mobility analyzer comprises a drift tube which is separated from the second ionization region by a shutter gate and further comprises a gas flow system that directs a gas flow from the drift tube through the second ionization region towards the first ionization region.

4. The ion mobility spectrometer according to claim 3, wherein an X-ray tube is located on the front side of the ion source such that radiation is emitted and passes through the first and the second ionization region along the axis of the drift tube.

5. The ion mobility spectrometer according to claim 3, wherein a radioactive source is located in the first and second ionization region.

6. The ion mobility spectrometer according to claim 1, wherein the ion transfer control system controls the transfer of calibrant ions from the second ionization region to the third region.

7. The ion mobility spectrometer according to claim 1, wherein the ion transfer system comprises at least one of a Bradbury-Nielson gate, a single aperture electrode, and a grid electrode.

8. The ion mobility spectrometer according to claim 1, wherein the ion transfer system comprises an ion gating element located at the exit of at least one of the first and second ionization regions.

9. The ion mobility spectrometer according to claim 1, wherein the ion transfer system comprises multiple aperture electrodes located along at least one of the first and second ionization regions for generating an electrical drift field therein.

10. The ion mobility spectrometer according to claim 1, wherein the calibrant reservoir is filled with at least one of a dicarboxylic acid and chlorovanilin.

11. A method for calibrating the mobility axis of an ion mobility spectrum acquired in an ion mobility spectrometer with an ion source and a mobility analyzer, comprising the steps of:
(a) providing a gas-phase substance from a sample source to a first ionization region of the ion source and a gas-phase calibrant to a second ionization region of the ion source, wherein the first and the second ionization regions are spatially separated;
(b) switching an electric potential applied to at least one electrode of the first ionization region to inhibit the transfer of sample ions from the first ionization region to one of the second ionization region and a third region of the ion source located closer to the mobility analyzer than the first and second ionization regions;
(c) acquiring a mobility spectrum of calibrant ions generated in the second ionization region wherein the mobility spectrum comprises substantially no signals of sample ions generated in the first ionization region; and
(d) determining a calibration function for the mobility axis from at least one signal of a calibrant ion species and the known mobility of the calibrant ion species.

12. The method according to claim 11, further comprising:
switching said electric potential to release ions from the first ionization region into the third region;
acquiring a mobility spectrum comprising signals of calibrant and sample ions; and
determining the mobility characteristic for at least one measured sample ion using the calibration function.

13. The method according to claim 11, further comprising:
switching the electric potential applied to the at least one electrode of the first ionization region to release ions from the first ionization region into the third region;
switching an electric potential applied to at least one electrode of the second ionization region such that the transfer of ions from the second ionization region into the third region of the ion source is inhibited;
acquiring a mobility spectrum comprising signals of sample ions only; and
determining the mobility characteristic for at least one measured sample ion using the calibration function.

14. The method according to claim 11, wherein the signal position of at least one reactant ion species generated in the second ionization region is utilized to adjust the calibration function with regard to the humidity of the gas in the mobility analyzer.

15. A method for calibrating the mobility axis of an ion mobility spectrum acquired in an ion mobility spectrometer having an ion source and a mobility analyzer, comprising the steps:
(a) providing a gas-phase substance from a sample source to a first ionization region of the ion source and a gas-phase calibrant to a second ionization region of the ion source, wherein the first and the second ionization region are spatially separated;
(b) switching an electric potential applied to at least one electrode of the second ionization region such that the transfer of calibrant ions from the second ionization region into the first ionization region is inhibited and acquiring a first mobility spectrum comprising substantially no signals of calibrant ions;
(c) switching said electric potential such that calibrant ions are released into the first ionization region and acquiring a second mobility spectrum comprising sample and calibrant ions; and
(d) determining a calibration function for the mobility axis from at least one signal of a calibrant ion species and a known mobility of the calibrant ion species.

\* \* \* \* \*